US 8,067,177 B2

(12) United States Patent
Mahoney et al.

(10) Patent No.: US 8,067,177 B2
(45) Date of Patent: Nov. 29, 2011

(54) AMPLIFICATION METHODS

(75) Inventors: Walt Mahoney, Woodinville, WA (US);
Nicolaas M. J. Vermeulen, Woodinville, WA (US); Irina Afonina, Mill Creek, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 0 days.

(21) Appl. No.: 12/725,922

(22) Filed: Mar. 17, 2010

(65) Prior Publication Data
US 2011/0027780 A1    Feb. 3, 2011

Related U.S. Application Data

(63) Continuation of application No. 11/958,895, filed on Dec. 18, 2007, now Pat. No. 7,723,038, which is a continuation of application No. 11/202,627, filed on Aug. 11, 2005, now Pat. No. 7,319,022.

(60) Provisional application No. 60/601,206, filed on Aug. 13, 2004.

(51) Int. Cl.
*C12P 19/34* (2006.01)
*C12Q 1/68* (2006.01)
*C07H 19/04* (2006.01)

(52) U.S. Cl. ....... 435/6.12; 435/6.1; 536/23.1; 536/26.6
(58) Field of Classification Search ............... 435/6.12, 435/6.1; 536/23.1, 26.6
See application file for complete search history.

(56) References Cited

FOREIGN PATENT DOCUMENTS
WO    WO 03/062445 A2    7/2003

OTHER PUBLICATIONS

Notice of Reasons for Rejection of Application No. 2007-525843, Japanese Patent Office.
Wittwer, et al., Real-Time Multiplex PCR Assays, Methods 25, 430-442 (2001).
Afonina, et al., Hybridization-triggered fluorescence detection of DNA with minor groove binder-conjugated probes, Proceedings of SPIE, vol. 4626 (2002).
Afonina, et al., Minor Groove Binder-Conjugated DNA Probes for Quantitative DNA Detection by Hybridization-Triggered Fluorescence, BioTechniques, vol. 32, No. 4 (2002).
Japanese Patent Office; Written Amendment, Japanese Application No. 2007-525843, Jul. 22, 2011.
Japanese Patent Office; Written Argument, Japanese Application No. 2007-525843, Jul. 22, 2011.

*Primary Examiner* — Jezia Riley
(74) *Attorney, Agent, or Firm* — Jackson Walker L.L.P.

(57) ABSTRACT

Methods are provided for amplification and monitoring of oligonucleotide amplification in which a primer has an overlap with one or more bases of a detection probe.

12 Claims, 5 Drawing Sheets

BK Virus Titration

AMPLIFICATION METHODS

CROSS-REFERENCES TO RELATED APPLICATIONS

This application is a continuation application of and claims the benefit of U.S. patent application Ser. No. 11/958895, entitled "Amplification Methods," filed Dec. 18, 2007, which is expressly incorporated herein by reference in its entirety, and which is a continuation application of and claims the benefit of U.S. patent application Ser. No. 11/202,627, now U.S. Pat. No. 7,319,022, entitled "Amplification Methods", filed Aug. 11, 2005, which is expressly incorporated herein by reference in its entirety, and which claims the benefit of U.S. Provisional Application Ser. No. 60/601,206 filed Aug. 13, 2004, the contents of which are incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Efficient PCR amplification is particularly required in biological applications in which highly sensitive and accurate detection is required. In most primer and probe design programs it is recommended that probes should be designed first and then primers should be designed close to the probes without overlapping sequences (e.g. Primer Express Software Version 2.0, Applied Biosystems, Foster City, Calif.). PCR amplification methods are widely used in the diagnostic industry. Unexpectedly, we discovered that overlapping primer and probe still give efficient PCR, expanding probe and primer design opportunities particularly in challenging sequence environments. The PCR method and its clinical applications have been disclosed (U.S. Pat. No. 4,683,202; Lynch J R, Brown J M. *J Med. Genet.*, 27:2-7 (1990); Yang S, Rothman R E. *Lancet Infect Dis.*, 4:337-48 (2004))

The schematic representation of the overlapping probe and primer in a novel amplification method of the invention is shown in FIG. 1. FIG. 1a) and b) show a schematic representation of primer and probe location on the target, with a primer sequence overlapping with a probe sequence. FIG. 1c) shows a schematic representation of two overlapping primer sequences. FIG. 1d) shows a schematic representation of a probe sequence overlapping with both primers.

5'-Minor groove binder (MB)-Quencher (O)-oligonucleotide-Fluorophore (Fl)-3' or 5'-MB-Fl-oligonucleotide-Q-3' or 5'-Fl-oligonucleotide-Q-MB-3' probes have not been overlapped with primers. It is suggested in the PCR amplification literature that "one should avoid complementarity at 3'-ends of primer pairs as this promotes the formation of primer-dimer artifacts and reduces the yield of the desired products (Innis, M. and Gelfand, D. Optimization of PCR in Innis, M., Gelfand, D., Sninsky, J. and White, T., Editors. PCR PROTOCOLS A GUIDE TO METHODS AND APPLICATIONS. Academic Press, San Diego, Calif. pages 3-12, 1989.) Since the probe and primer have overlapping complementary sequences and available 3' sequences, it was expected the 5'-MB-Q-oligonucleotide-Fl-3' or 5'-MB-Fl-oligonucleotide-Q-3' or 5'-Fl-oligonucleotide-Q-MB-3' probes overlapping with a primer would give poor amplification. However, unexpectedly it was observed that efficient amplification occurs in the case of FIG. 1b. Without being bound to a theory, we suspect that the probe containing a MB ligand, Q and a Fl has a tight conformation in solution where these components are in close proximity. We have shown that such a probe in solution is quenched from temperatures ranging from 25 to 95° C., suggesting that overlaps from 1 to about 7 bases are not enough to overcome the in solution stable conformation of the probe to allow hydrogen bond formation. In FIG. 1a the Primer-Probe dimer should not give rise to any artifacts. The 3'-end is not available for priming. Surprisingly, this type of design can provide good amplification.

BRIEF SUMMARY OF THE INVENTION

The present invention describes the method where the oligonucleotide probe and an oligonucleotide primer sequences are overlapping with about one to about 7 bases in a polymerase-based amplification. The probes and primers of the invention are optionally modified oligonucleotides. In one group of embodiments, the primer sequences are overlapping and the amplified target is detected, either indirectly or with a DNA binding agent.

The primers and probes of the invention are oligonucleotides of about 5 to 40 bases, more preferably 5 to 30 bases, with the proviso that they are compatible with the polymerase amplification.

In one embodiment of the invention the oligonucleotide primers and probes contain the natural bases, namely guanine, cytosine, adenine, thymine or uracil In another embodiment the probes and primers of the invention contain one or more non-natural, promiscuous or universal base.

In another embodiment the probe is a fluorescence resonance transfer probe (FRET), containing a fluorophore with emission wavelengths from about 400 nm to about 900 nm and a quencher with an absorbance wavelengths from about 400 nm to about 900 nm. Fluorophores and quenchers are available from commercial resource (eg. Molecular Probes, Eugene, Oreg.; Epoch Bioscience, Bothell, Wash.). Typically the probes are from about 8 to 30 bases long.

In yet another embodiment the difference in thermodynamic properties ($\Delta G$) is large enough to allow substantial overlap of probe and primer sequences in PCR amplification.

In yet another embodiment the detection FRET probe contains a minor groove binder, fluorophore and quencher. The preferred probe conjugates have the formula shown in Formula I, where $Fl^A$ and $Fl^B$ can be either a fluorophore or a quencher with the proviso that the conjugate contains at least one quencher and at least one fluorophore and n is 0 or 1.

Formula I a)
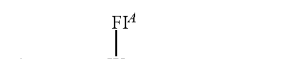

b)
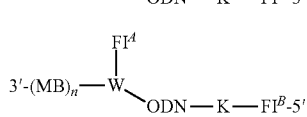

In a related embodiment the two primers overlap from 1 to 7 bases. The amplified target is detected by a nucleic-acid-binding reagent. Alternatively the amplified material can be detected indirectly by using a biotinylated primer and enzymatic detection known in the art.

In yet another embodiment, the overlapping primer and probe are used in amplification of targets with continuous probe monitoring. In yet another embodiment the overlapping primer and probe are used to amplify closely related targets for mismatch discrimination using at least one probe. Related targets are those in which the target sequences differ by from one to three mismatches, preferably one or two mismatches. In some embodiments single nucleotide polymorphisms are determined by post amplification melting curve analysis by measuring the fluorescence emission dependence of each probe with temperature.

In a related embodiment the overlapping primer and probe are used to amplify nucleic acid targets for fluorescent probe endpoint detection.

DETAILED DESCRIPTION OF THE INVENTION

Figure 1:
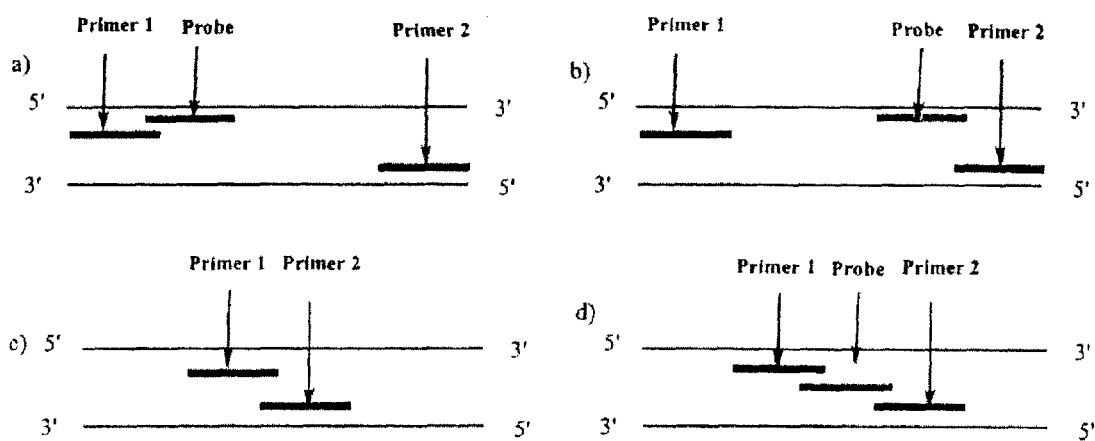
FIG. 1 provides a schematic representation of primer and probe location on a target, with a primer sequence overlapping a probe sequence (FIGS. 1a and 1b), primer-primer overlap (FIG. 1c) and probe overlap with two primer sequences (FIG. 1d).

As noted above, the present invention provides amplification methods and hybridization methods wherein an oligonucleotide probe and an oligonucleotide primer have sequences that are overlapping with about one to about 7 bases in a polymerase-based amplification. The probes and primers of the invention are optionally modified oligonucleotides. Generally, the primers and probes of the invention are oligonucleotides of about 5 to 40 bases, more preferably 5 to 30 bases, which are compatible with the polymerase amplification. In a number of embodiments, the oligonucleotide primers and probes contain the natural bases, namely guanine, cytosine, adenine, thymine or uracil; while in other embodiments, the probes and primers of the invention contain one or more non-natural, promiscuous or universal bases. In some embodiments, the overlap between an oligonucleotide probe and an oligonucleotide primer, or between two primers is shorter than the length of the primer or primers.

In another embodiment the probe is a fluorescence resonance transfer probe (FRET), containing a fluorophore with an emission wavelength from about 400 nm to about 900 nm and quencher with an absorbance wavelength from about 400 nm to about 900 nm. Fluorophores and quenchers are available from commercial resource (eg. Molecular Probes, Eugene, Oreg.; Epoch Bioscience, Bothell, Wash.). Typically the probes are from about 8 to 40 bases in length, and in some embodiments, the probes are from about 8 to 30 bases in length.

In yet another embodiment the difference in thermodynamic properties (ΔG) is large enough to allow substantial overlap of probe and primer sequences in PCR amplification.

In yet another embodiment the FRET probe contains a minor groove binder, fluorophore and quencher. The preferred probe conjugates have the formula shown in Formula I, where $Fl^A$ and $Fl^B$ can be either a fluorophore or a quencher such that the conjugate contains only one quencher and one fluorophore and n is 0 or 1.

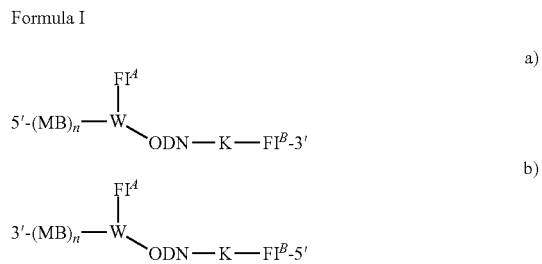

Formula I

Oligonucleotides and Modified Oligonucleotides

The terms oligonucleotide, polynucleotide and nucleic acid are used interchangeably to refer to single- or double-stranded polymers of DNA or RNA (or both) including polymers containing modified or non-naturally-occurring nucleotides, or to any other type of polymer capable of stable base-pairing to DNA or RNA including, but not limited to, peptide nucleic acids which are disclosed by Nielsen et al. Science 254:1497-1500 (1991); bicyclo DNA oligomers (Bolli et al., Nucleic Acids Res. 24:4660-4667 (1996)) and related structures. For the conjugates used in the present invention, a minor groove binder (MB) moiety is attached to either the 3' or the 5' end of the oligonucleotide probe and a quencher or fluorescent label is attached at the 3' end, the 5' end, or in an internal portion of the oligonucleotide probe.

Preferred in the present method invention are DNA oligonucleotides that are single-stranded and have a length of 100 nucleotides or less, more preferably 40 nucleotides or less, still more preferably 30 nucleotides or less and most preferably 20 nucleotides or less with a lower limit being approximately 5 nucleotides.

Oligonucleotide primers and oligonucleotide conjugates containing a fluorophore/quencher pair with a minor groove binder may also comprise one or more modified bases, in addition to the naturally-occurring bases adenine, cytosine, guanine, thymine and uracil. Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7 deazapurines and their derivatives and pyrazolopyrimidines (described in PCT WO 01/84958); and also described in U.S. Pat. No. 6,127,121.

The most preferred modified bases for use in the present invention include the guanine analogue 6 amino 1H-pyrazolo[3,4 d]pyrimidin 4(5H)one (ppG or PPG, also Super G) and the adenine analogue 4 amino 1H-pyrazolo[3,4 d]pyrimidine (ppA or PPA). The xanthine analogue 1H-pyrazolo[5,4 d]pyrimidin 4(5H)-6(7H)-dione (ppX) can also be used. These base analogues, when present in an oligonucleotide, strengthen hybridization and improve mismatch discrimination. All tautomeric forms of naturally-occurring bases, modified bases and base analogues may be included in the oligonucleotide conjugates of the invention. Other modified bases useful in the present invention include 6-amino-3-prop-1-ynyl-5-hydropyrazolo[3,4-d]pyrimidine-4-one, PPPG; 6-amino-3-(3-hydroxyprop-1-ynyl)-5-hydropyrazolo[3,4-d]pyrimidine-4-one, HOPPPG; 6-amino-3-(3-aminoprop-1-ynyl)-5-hydropyrazolo[3,4-d]pyrimidine-4-one, NH2PPPG; 4-amino-3-(prop-1-ynyl)pyrazolo[3,4-d]pyrimidine, PPPA; 4-amino-3-(3-hydroxyprop-1-ynyl)pyrazolo[3,4-d]pyrimidine, HOPPPA; 4-amino-3-(3-aminoprop-1-ynyl)pyrazolo[3,4-d]pyrimidine, NH$_2$PPPA; 3-prop-1-ynylpyrazolo[3,4-d]pyrimidine-4,6-diamino, (NH$_2$)$_2$PPPA; 2-(4,6-diaminopyrazolo[3,4-d]pyrimidin-3-yl)ethyn-1-ol, (NH$_2$)$_2$ PPPAOH; 3-(2-aminoethynyl)pyrazolo[3,4-d]pyrimidine-4,6-diamine, $(NH_2)_2$PPPANH$_2$; 5-prop-1-ynyl-1,3-dihydropyrimidine-2,4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1,3-dihydropyrimidine-2-one, $NH_2$PC; 5-[4-amino-3-(3-methoxyprop-1-ynyl)pyrazol[3,4-d]pyrimidinyl]-2-(hydroxymethyl)oxolan-3-ol, $CH_3$OPPPA; 6-amino-1-[4-hydroxy-5-(hydroxymethyl)oxolan-2-yl]-3-(3-methoxyprop-1-ynyl)-5-hydropyrazolo[3,4-d]pyrimidin-4-one, $CH_3$OPPPG; 4,(4,6-Diamino-1H-pyrazolo[3,4-d]pyrimidin-3-yl)-but-3-yn-1-ol, Super A; 6-Amino-3-(4-hydroxy-but-1-ynyl)-1,5-dihydro-pyrazolo[3,4-d]pyrimidin-4-one; 5-(4-hydroxy-but-1-ynyl)-1H-pyrimidine-2,4-dione, Super T; 3-iodo-1H-pyrazolo[3,4-d]pyrimidine-4,6-diamine ($(NH_2)_2$PPAI); 3-bromo-1H-pyrazolo[3,4-d]pyrimidine-4,6-diamine ($(NH_2)_2$PPABr); 3-chloro-1H-pyrazolo[3,4-d]pyrimidine-4,6-diamine ($(NH_2)_2$PPACl); 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-chloro-1H-pyrazolo[3,4-d]pyrimidin-4-ylamine (PPACl).

In addition to the modified bases noted above, the oligonucleotides of the invention can have a backbone of sugar or glycosidic moieties, preferably 2-deoxyribofuranosides wherein all internucleotide linkages are the naturally occurring phosphodiester linkages. In alternative embodiments however, the 2-deoxy-β-D-ribofuranose groups are replaced with other sugars, for example, β-D-ribofuranose. In addition, β-D-ribofuranose may be present wherein the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl)ribose), or is replaced by a fluoro group (2-fluororibose). Related oligomer-forming sugars useful in the present invention are those that are "locked", i.e., contain a methylene bridge between C-4' and an oxygen atom at C-2'. Other sugar moieties compatible with hybridization of the oligonucleotide can also be used, and are known to those of skill in the art, including, but not limited to, α-D-arabinofuranosides, α-2'-deoxyribofuranosides or 2',3'-dideoxy-3'-aminoribofuranosides. Oligonucleotides containing α-D-arabinofuranosides can be prepared as described in U.S. Pat. No. 5,177,196. Oligonucleotides containing 2',3'-dideoxy-3'-aminoribofuranosides are described in Chen et al. *Nucleic Acids Res.* 23:2661-2668 (1995). Synthetic procedures for locked nucleic acids (Singh et al, *Chem. Comm.,* 455-456 (1998); Wengel J., *Acc. Chem. Res.,* 32:301-310 (1998)) and oligonucleotides containing 2'-halogen-2'-deoxyribofuranosides (Palissa et al., *Z. Chem.,* 27:216 (1987)) have also been described. The phosphate backbone of the modified oligonucleotides described herein can also be modified so that the oligonucleotides contain phosphorothioate linkages and/or methylphosphonates and/or phosphoroamidates (Chen et al., *Nucl. Acids Res.,* 23:2662-2668 (1995)). Combinations of oligonucleotide linkages are also within the scope of the present invention. Still other backbone modifications are known to those of skill in the art.

In another group of embodiments, the modified bases described herein are incorporated into PNA and DNA/PNA chimeras to balance $T_m$s and provide modified oligonucleotides having improved mismatch discrimination. Various modified forms of DNA and DNA analogues have been used in attempts to overcome some of the disadvantages of the use of DNA molecules as probes and primers. Among these are peptide nucleic acids (PNAs, also known as polyamide nucleic acids). Nielsen et al. *Science* 254:1497-1500 (1991). PNAs contain heterocyclic base units, as found in DNA and RNA, that are linked by a polyamide backbone, instead of the sugar-phosphate backbone characteristic of DNA and RNA. PNAs are capable of hybridization to complementary DNA and RNA target sequences and, in fact, hybridize more strongly than a corresponding nucleic acid probe. The synthesis of PNA oligomers and reactive monomers used in the synthesis of PNA oligomers have been described in U.S. Pat. Nos. 5,539,082; 5,714,331; 5,773,571; 5,736,336 and 5,766,855. Alternate approaches to PNA and DNA/PNA chimera synthesis and monomers for PNA synthesis have been summarized. Uhlmann et al. *Angew. Chem. Int. Ed.* 37:2796-2823 (1998). Accordingly, the use of any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal bases, sugar modification, backbone modification or a minor groove binder to balance the $T_m$ of a DNA, PNA or DNA/PNA chimera is in the scope of this invention. The synthetic methods necessary for the synthesis of modified base monomeric units required for nucleic acid, PNA and PNA/DNA chimeras synthesis are available in the art, see methods in this application and Uhlmann et al. *Angew. Chem. Int. Ed.* 37:2796-2823 (1998).

For the uses described herein, and as noted above, the oligonucleotides and modified oligonucleotides will preferably have from 5 to 100 bases, more preferably from 5 to 40 bases, still more preferably, 5 to 30 bases, and even more preferably, 5 to 20 bases. In some embodiments, the oligonucleotide portions of the probes/conjugates will have 5 to 15 bases. In some embodiments, the oligonucleotide portions will have 6, 7, 8, 9, 10, 11, 12, 13 or 14 bases or modified bases.

The ability to design probes and primers for the invention method in a predictable manner using an algorithm, that can direct the use or incorporation of modified bases, minor groove binders, fluorphores and/or quenchers, based on their thermodynamic properties have been described in U.S. Pat. No. 6,683,173. Accordingly, the use of any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal bases, sugar modification, backbone modification or a minor groove binder to balance the $T_m$ (e.g., within about 5-8° C.) of a hybridized product with a nucleic acid, PNA or DNA/PNA chimera is contemplated by the present invention.

Minor Groove Binders

The probes/conjugates used in the method of the present invention will optionally have a covalently attached minor groove binder (MB). A variety of suitable minor groove binders have been described in the literature. See, for example, Kutyavin, et al. U.S. Pat. No. 5,801,155; Wemmer, D. E., and Dervan P. B., *Current Opinion in Structural Biology,* 7:355-361 (1997); Walker, W. L., Kopka, J. L. and Goodsell, D. S., *Biopolymers,* 44:323-334 (1997); Zimmer, C & Wahnert, U. *Prog. Biophys. Malec. Bio.* 47:31-112 (1986) and Reddy, B. S. P., Dondhi, S. M., and Lown, J. W., Pharmacol. Therap., 84:1-111 (1999).

Suitable methods for attaching MBs (as well as reporter groups such as fluorophores and quenchers described below) through linkers to oligonucleotides are described in, for example, U.S. Pat. Nos. 5,512,677; 5,419,966; 5,696,251; 5,585,481; 5,942,610 and 5,736,626.

The MB is generally attached to the 5' position of the oligonucleotide portion via a suitable linking group, although attachment can be made to other positions on the oligonucleotide portion. Attachment at the 5' end provides both a benefit of hybrid stability, since melting of an oligonucleotide duplex begins at the termini, but also reduces and/or prevents nuclease digestion of the probe during amplification reactions.

The location of a MB within an MB oligonucleotide conjugate can also affect the discriminatory properties of such a conjugate. An unpaired region within a duplex will result in changes in the shape of the minor groove in the vicinity of the mispaired base(s). Since MBs fit best within the minor groove of a perfectly-matched DNA duplex, mismatches resulting in shape changes in the minor groove would reduce binding strength of a MB to a region containing a mismatch. Hence, the ability of a MB to stabilize such a hybrid would be decreased, thereby increasing the ability of a MB oligonucleotide conjugate to discriminate a mismatch from a perfectly matched duplex. On the other hand, if a mismatch lies outside of the region complementary to a MB oligonucleotide conjugate, discriminatory ability for unconjugated and MB-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of MB oligonucleotides conjugates in this context lies in the fact that much shorter oligonucleotides compared to those used previously (i.e., 20 mers or shorter) having greater discriminatory powers, can be used, due to the pronounced stabilizing effect of MGB conjugation.

In one group of embodiments, the MB is selected from the group consisting of CC1065 analogs, lexitropsins, distamycin, netropsin, berenil, duocarmycin, pentamidine, 4,6-diamino-2-phenylindole and pyrrolo[2,1 c][1,4]benzodiazepines.

Further preferred minor groove binders are those selected from the formulae:

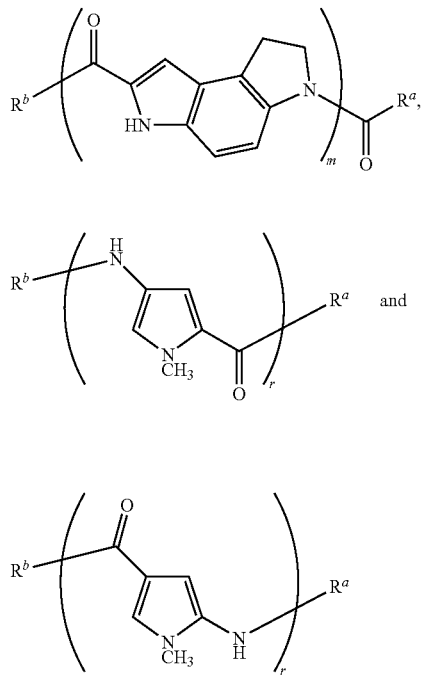

the subscript m is an integer of from 2 to 5; the subscript r is an integer of from 2 to 10; and each $R^a$ and $R^b$ is independently a linking group to the oligonucleotide (either directly or indirectly through a quencher), H, —$OR^c$, —$NR^cR^d$, —$COOR^c$ or —$CONR^cR^d$, wherein each $R^c$ and $R^d$ is selected from H, ($C_1$-$C_{12}$)heteroalkyl, ($C_2$-$C_{12}$)heteroalkenyl, ($C_2$-$C_{12}$)heteroalkynyl, ($C_1$-$C_{12}$)alkyl, ($C_2$-$C_{12}$)alkenyl, ($C_2$-$C_{12}$)alkynyl, aryl($C_1$-$C_{12}$)alkyl and aryl, with the proviso that one of $R^a$ and $R^b$ represents a linking group to ODN, Fl or Q.

Particularly preferred minor groove binders include the trimer of 3-carbamoyl-1,2-dihydro-(3H)-pyrrolo[3,2-e]indole-7-carboxylate ($CDPI_3$), the pentamer of N-methylpyrrole-4-carbox-2-amide ($MPC_5$) and other minor groove binders that exhibit increased mismatch discrimination. Additional MG moieties that will find use in the practice of the present invention are disclosed in co-owned U.S. Pat. No. 5,801,155. In certain embodiments, the MBs can have attached water solubility-enhancing groups (e.g., sugars, amino acids, carboxylic acid or sulfonic acid substituents, and the like). See PCT/US03/07467. Dihydrocyclopyrroloindole tripeptide ($DPI_3$) oligonucleotides conjugates are marketed by Epoch Biosciences as MGB ECLIPSE PROBE SYSTEMS. MGB™ is a trademark of Epoch Biosciences (Bothell, Wash.).

Quenchers

Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance ($R_o$) is described as the distance between the donor and acceptor molecules where the energy transfer is 50% efficient. Other mechanisms of fluorescence quenching are also known, such as, collisional and charge transfer quenching. There is extensive guidance in the art for selecting quencher and fluorophore pairs and their attachment to oligonucleotides (Haugland, R. P., HANDBOOK OF FLUORESCENT PROBES AND RESEARCH CHEMICALS, Sixth Edition, Molecular Probes, Eugene, Oreg., 1996; U.S. Pat. Nos. 3,996,345 and 4,351,760 and the like). Preferred quenchers are described in co-owned U.S. Pat. No. 6,727,356, and incorporated herein by reference. More particularly, Table 1 below contains structures of quenchers that can be readily modified to structures having suitable functional groups (e.g., $Fl^A$-W where $FL^A$ is a quencher, with attachment sites for ODN and MB portions) for introduction into probes, based on the known chemical reactions cited (see, for example, Thiel, et al., *J. fur prakt. Chemie*, 328:497-514 (1986); U.S. Pat. Nos. 4,324,721 and 4,054,560; Timm, *Melliand Textilberichte*, 9:1090-1096 (1969); Hallas, *J.S.D.C.* 285-294 (1979); Beyer, et al., *J Prakt. Chem.*, 24:100-104 (1964); Hutchings, et al., *Chem. Europ. J.* 3:1719-1727 (1997) and Morley, et al., *J. Phys. Chem. A.*, 102:5802-5808 (1998); Haak, et al., *J. Chem. Res. Miniprint* 10:2701-2735 (1998) and Ruggli et al., *Helv. Chim. Acta*, 26:814-826 (1943). Additional structures (e.g., mono- and bis-azo dyes) with different combinations of substituents at various positions can be prepared based on compounds and methods known in the dye chemistry field (summarized in the Color Index, Issue 3 on CDD-ROM, pages 4009-4324; Society of Dyers and Colourists, Bradford, England; http://www.sdc.org.uk; and see also WO 01/86001).

TABLE 1

| Structure Literature | $\lambda_{max}$ nm; $\epsilon$ M$^{-1}$cm$^{-1}$; Solvent | Linker-Modified Structure Q—W |
|---|---|---|
| [allyl-methylamino-phenyl-azo-phenyl-CH=CH-(4-nitro-2-cyanophenyl)] | 464 | [bis(hydroxyethyl)amino-phenyl-azo-phenyl-CH=CH-(4-nitro-2-cyanophenyl)] |
| [phenyl-azo-biphenyl-NO$_2$] | 440 | [bis(hydroxyethyl)amino-phenyl-azo-biphenyl-NO$_2$] |
| [diethylamino-phenyl-azo-(2-nitro-4-nitrophenyl)] | 540; 40,000 MeOH | [bis(hydroxyethyl)amino-phenyl-azo-(2-nitro-4-nitrophenyl)] |
| [diethylamino-phenyl-azo-(2-nitro-4-nitro-6-bromophenyl)] | 549; 37,000 EtOH | [bis(hydroxyethyl)amino-phenyl-azo-(2-nitro-4-nitro-6-bromophenyl)] |

TABLE 1-continued

| Structure Literature | $\lambda_{max}$ nm; $\epsilon$ M$^{-1}$cm$^{-1}$; Solvent | Linker-Modified Structure Q—W |
|---|---|---|
| | 590 48,978 CHCl$_3$ | |
| | 601 40,738 CHCl$_3$ | |
| | 623 48,000 CHCl$_3$ | |
| | 656 100,000 CHCl$_3$ | |

TABLE 1-continued

| Structure Literature | $\lambda_{max}$ nm; $\epsilon$ M$^{-1}$cm$^{-1}$; Solvent | Linker-Modified Structure |
|---|---|---|
| | | Q—W |
| | 656 53,043 | |
| | 598 | |
| | 582 | |
| | 652 | |

TABLE 1-continued

| Structure Literature | $\lambda_{max}$ nm; $\epsilon$ M$^{-1}$cm$^{-1}$; Solvent | Linker-Modified Structure Q—W |
|---|---|---|
| | 554 50,000 | |
| | 673.5 | |
| | 809 | |

TABLE 1-continued

| Structure Literature | $\lambda_{max}$ nm; $\epsilon$ M$^{-1}$cm$^{-1}$; Solvent | Linker-Modified Structure Q—W |
|---|---|---|
| [structure] | 592<br>46,000 | [structure] |
| [structure] | 601<br>51,000 | [structure] |
| [structure] | 623<br>48,000 | [structure] |
| [structure] | 632<br>Predicted | [structure] |

The quenchers above cover the range from about 400-800 mm, and many demonstrate improved quenching when attached to a MB. While the modified versions illustrate —N(CH$_2$CH$_2$OH)$_2$ as a preferred linking group to be used to couple the quencher to oligonucleotides, MB or solid support, examples of other suitable linkers are known in the art or are provided herein.

Preferred quenchers for each of the aspects of the invention herein are selected from those in the table above, as well as bis azo quenchers from Biosearch Technologies, Inc. (provided as BLACK HOLE™ Quenchers: BH-1, BH-2 and BH-3), Dabcyl, TAMRA and carboxytetramethyl rhodamine.

Fluorophores

Fluorophores useful in the present invention are generally fluorescent organic dyes that have been derivatized for attachment to the terminal 3' or 5' position of the oligonucleotide probe, preferably via a linking group. One of skill in the art will appreciate that suitable fluorophores are selected in combination with a quencher which is typically also an organic dye, which may or may not be fluorescent.

There is a great deal of practical guidance available in the literature for selecting appropriate fluorophore-quencher pairs for particular probes. See, for example, Clegg (cited above); Wu et al. (cited above); Pesce et al., editors, FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic (quenching) molecules and their relevant optical properties for choosing fluorophore-quencher pairs, e.g., Berlman, HANDBOOK OF FLUORESCENCE SPECTRA OF AROMATIC MOLECULES, 2ND EDITION (Academic Press, New York, 1971); Griffiths, COLOUR AND CONSTITUTION OF ORGANIC MOLECULES (Academic Press, New York, 1976); Bishop, editor, INDICATORS (Pergamon Press, Oxford, 1972); Haugland, THE HANDBOOK, A GUIDE TO FLUORESCENT PROBES AND LABELING TECHNOLOGIES (Invitrogen, Eugene, Ore. 2005); Pringsheim, FLUORESCENCE AND PHOSPHORESCENCE (Interscience Publishers, New York, 1949); and the like. Additionally, methods for derivatizing fluorophores and quenchers for covalent attachment via common reactive groups are also well known. See, for example, Haugland (cited above); Ullman et al., U.S. Pat. No. 3,996,345; Khanna et al., U.S. Pat. No. 4,351,760; and the like.

Preferred fluorophores are those based on xanthene dyes, a variety of which are available commercially with substituents useful for attachment of either a linking group or for direct attachment to an oligonucleotide. Another group of fluorescent compounds are the naphthylamines, having an amino group in the α- or β-position. Included among such naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like. Still other suitable fluorophores include the resorufin dyes, rhodamine dyes, cyanine dyes and BODIPY dyes.

These dyes and appropriate linking methodologies for attachment to oligonucleotides are described in many references, e.g., Khanna et al. (cited above); Marshall, *Histochemical J.*, 7:299-303 (1975); Menchen et al., U.S. Pat. No. 5,188,934; Menchen et al., European Patent Application 87310256.0; and Bergot et al., WO 9105060.

More particularly, the fluorophores described herein can be attached to the oligonucleotide portions using, for example, chemical or enzymatic methods. By way of example, methods for incorporation of reactive chemical groups into oligonucleotides, at specific sites, are well-known to those of skill in the art. Oligonucleotides containing a reactive chemical group, located at a specific site, can be combined with a label attached to a complementary reactive group (e.g., an oligonucleotide containing a nucleophilic reactive group can be reacted with a label attached to an electrophilic reactive group) to couple a label to a probe by chemical techniques. Exemplary labels and methods for attachment of a label to an oligonucleotide are described, for example, in U.S. Pat. Nos. 5,824,796; 5,210,015; Kessler (ed.), *Nonradioactive Labeling and Detection of Biomolecules*, Springer-Verlag, Berlin, 1992; Kricka (ed.) *Nonisotopic DNA Probe Techniques*, Academic Press, San Diego, 1992; Howard (ed.) *Methods in Nonradioactive Detection*, Appleton & Lange, Norwalk, 1993. Non-specific chemical labeling of an oligonucleotide can be achieved by combining the oligonucleotide with a chemical that reacts, for example, with a particular functional group of a nucleotide base, and simultaneously or subsequently reacting the oligonucleotide with a label. See, for example, Draper et al. (1980) *Biochemistry* 19:1774-1781. Enzymatic incorporation of label into an oligonucleotide can be achieved by conducting enzymatic modification or polymerization of an oligonucleotide using labeled precursors, or by enzymatically adding label to an already-existing oligonucleotide. See, for example, U.S. Pat. No. 5,449,767. Examples of modifying enzymes include, but are not limited to, DNA polymerases, reverse transcriptases, RNA polymerases, etc. Examples of enzymes which are able to add a label to an already-existing oligonucleotide include, but are not limited to, kinases, terminal transferases, ligases, glycosylases, etc.

For each of the aspects of the present invention, preferred fluorophores are selected from cyanines, BODIPY analogs, 5-FAM, 6-FAM, TET™, JOE™ HEX™, VIC™, NED™, TAMRA™, ROX™, Bothell Blue™ and Yakima Yellow™ (YY). These fluorophores are generally available from commercial sources such as Applied Biosystems Inc., Foster City, Calif. and Epoch Biosciences, Inc., Bothell, Wash.

Homogeneous methods for amplified nucleic acid detection with nucleic acid binding reagents have been disclosed (see, U.S. Pat. Nos. 5,994,056 and 6,171,785; and Bengtsson et al. *Nucl. Acids Res.*, 31:e45 (2003)). CYBR® Green I a DNA binding agent has been used for monitoring amplification (U.S. Pat. No. 6,569,627). Nucleic-binding dyes are commercially available from, for example, Invitrogen (Eugene, Oreg.; http://probes.invitrogen.com).

Linking Groups

A variety of linking groups and methods are known to those of skill in the art for attaching fluorophores, quenchers and minor groove binders to the 5' or 3' termini of oligonucleotides. See, for example, Eckstein, editor, OLIGONUCLEOTIDES AND ANALOGUES: A PRACTICAL APPROACH (IRL Press, Oxford, 1991); Zuckerman et al., *Nucleic Acids Research*, 15:5305-5321 (1987); Sharma et al., *Nucleic Acids Research*, 19:3019 (1991); Giusti et al., *PCR Methods and Applications*, 2:223-227 (1993), Fung et al., U.S. Pat. No. 4,757,141; Stabinsky, U.S. Pat. No. 4,739,044; Agrawal et al., *Tetrahedron Letters*, 31:1543-1546 (1990); Sproat et al., *Nucleic Acids Research*, 15:4837 (1987); Nelson et al., *Nucleic Acids Research*, 17:7187-7194 (1989); and the like. Still other commercially available linking groups can be used that can be attached to an oligonucleotide during synthesis, e.g., available from Clontech Laboratories (Palo Alto, Calif.). Other methodologies for attaching a fluorophore to an oligonucleotide portion involve the use of phosphoramidite chemistry at the conclusion of solid phase synthesis by way of dyes derivatized with a phosphoramidite moiety. See, for example, Woo et al., U.S. Pat. No. 5,231,191; Hobbs, Jr., U.S. Pat. No. 4,997,928; Reed, et al., PCT publication No. WO 01/42505; U.S. Ser. No. 09/876,830; U.S. Pat. No. 6,653,473; and co-owned and pending U.S. Ser. No. 10/026,374.

While a number of general linking methods are available, the selection of certain linking groups constitute one aspect of the invention, when selection is made in combination with other factors such as oligonucleotide length, minor groove binders, fluorophore-quencher pairs, and the like. For example, in the present invention, the use of minor groove binders allows the preparation of probes having fewer nucleotide bases. In general, probes having fewer than about 15 bases have been considered unusable due to poor signaling and/or hybridization to target polynucleotides. Additionally, smaller probes (e.g., those of 15 or fewer bases) have been avoided for beacon assays as the quencher/fluorophore often are not sufficiently separated to provide a suitable signal upon hybridization.

In the present invention, shorter probes having attached minor groove binders are found to be useful, and sufficient spacing between the fluorophore and quencher can be obtained by selection of an appropriate linking group. The probes and conjugates will generally have one or two types of linking groups. As provided in formula I, the letter K represents a divalent linking group, while the letter W represents a trivalent linking group. The particular linking groups are generally selected for their ease of synthesis, utility in solid phase synthesis, stability during probe construction and use, and the physical parameters each imparts to the probe or conjugate such as providing adequate separation between the fluorophore and the quencher; or providing a tether of suitable length to allow the minor groove binder portion to non-covalently interact with the minor groove formed upon probe hybridization.

More particularly, K is a direct bond between a fluorophore and the oligonucleotide portion of the probe/conjugate, or is a divalent linking group having from 1 to 50 main chain atoms that are selected from C, O, N, S, P and Si.

The trivalent linking group W can encompass a variety of structures in order to provide suitable attachment and flexibility between the ODN, Q and MGB. In one group of embodiments, W is a trivalent functionality having the formula:

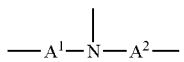

wherein the nitrogen atom is directly attached to an aromatic ring of a mono azo- or bis azo-dye (quencher, Q) and typically considered as part of the quencher, and the components $A^1$ and $A^2$ are independently selected from a bond or a linking/spacer portion having from 1 to about 50 atoms selected from C, N, S, P, Si and O, and additional hydrogen atoms to fill the available valences. Additionally, each of $A^1$ and $A^2$ can have cyclic components, acyclic (linear or branched) components, or a combination thereof.

Methods of Use

The method of the present invention where probe and primer sequences overlap provide advantages over existing methods, including an expansion of the primer and probe design opportunities especially in challenging sequences environments. The method of the invention is particularly useful performed in real-time with an amplification process such as, for example, PCR. The method of the present invention can be performed in a variety of formats including, but not limited to, a hybridization detection-based format, a format where the probe is cleaved by 5'-nuclease activity, or in a probe-independent format where the primers overlap and a double strand nucleic acid-specific dye is used to detect amplified target.

In one embodiment the probe and primer sequences are substantially overlapped, preferably between 1 and 20 bases, more preferably between 1 and 10 bases, and most preferred between 1 and 7 bases.

In methods of the present invention, probe and primer sequences overlap is useful in techniques in which hybridization of an oligonucleotide probe to another nucleic acid is involved. These include, but are not limited to, techniques in which hybridization of an oligonucleotide to a target nucleic acid is the endpoint; techniques in which hybridization of one or more oligonucleotides to a target nucleic acid precedes one or more polymerase-mediated elongation steps which use the oligonucleotide as a primer and the target nucleic acid as a template; techniques in which hybridization of an oligonucleotide to a target nucleic acid is used to block extension of another primer; and techniques in which two or more oligonucleotides are hybridized to a target nucleic acid and interactions between the multiple oligonucleotides are measured. Conditions for hybridization of oligonucleotides, and factors which influence the degree and specificity of hybridization, such as temperature, ionic strength and solvent composition, are well-known to those of skill in the art. See, for example, Sambrook et al., supra; Ausubel, et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al. (1991) *Nucleic Acids Res.* 19:5143-5151. In still other methods, multiple probes can be used to detect alternate target site regions (e.g., to identify difficult sequences or to differentiate species and subspecies of the target).

Hybridization of probes and/or primers to target sequences proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide which is complementary along its entire length with a target sequence is said to be perfectly complementary, perfectly matched, or fully complementary to the target sequence, and vice versa. An oligonucleotide and its target sequence can have related sequences, wherein the majority of bases in the two sequences are complementary, but one or more bases are noncomplementary, or mismatched. In such a case, the sequences can be said to be substantially complementary to one another. If the sequences of an oligonucleotide and a target sequence are such that they are complementary at all nucleotide positions except one, the oligonucleotide and the target sequence have a single nucleotide mismatch with respect to each other.

Hybridization based signal probes are well known in the art and include molecular beacons (U.S. Pat. No. 6,037,130), peptide nucleic acid beacons (U.S. Pat. No. 6,355,421) and 5'-minor groove binder probes, (WO03/062445, U.S. Pat. No. 6,472,153, and U.S. application Ser. No. 10/976,365) and fluorescent energy transfer probes (see, U.S. Pat. Nos. 6,911, 310 and 6,174,670). Self-reporting primers include self-quenched primers (Nazerenko et al, *Nucl. Acids Res.*, 30:e37 (2002)), duplex scorpion primers (Solinas et al, *Nucl. Acids Res.*, 29:e96 (2001)), Sunrise primers (Nazarenko et al. *Nucl. Acids Res.*, 25:2516-2521 (1997)) and PNA/DNA primers (Fiandaca et al, *Genome Res.*, 11:609-13 (2001)).

For those primer and probes used in the invention method which incorporate modified bases, it is understood that the modified bases will retain the base-pairing specificity of their naturally-occurring analogues. For example, PPPG analogues are complementary to cytosine, while PPPA analogues are complementary to thymine and uracil. The PPPG and PPPA analogues not only have a reduced tendency for so-called "wobble" pairing with non-complementary bases, compared to guanine and adenine, but the 3-substituted groups increase binding affinity in duplexes. Similarly, modified pyrimidines hybridize specifically to their naturally occurring counter partners.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, concentration of organic solvents such as formamide and dimethylsulfoxide and chaotropes.

Thus, in the formation of hybrids (duplexes) between a probe/conjugate and its target sequence, the probe/conjugate is incubated in solution, together with a polynucleotide containing the target sequence, under conditions of temperature, ionic strength, pH, etc, that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization of an oligonucleotide to a target sequence, also known as hybridization strength, is determined by methods that are well-known in the art. A preferred method is to determine the $T_m$ of the hybrid duplex. This is accomplished, as described supra, by subjecting a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature midpoint of the transition in ultraviolet absorbance that accompanies denaturation. Alternatively, if $T_m$s are known, a hybridization temperature (at fixed ionic strength, pH and solvent concentration) can be chosen that it is below the $T_m$ of the desired duplex and above the $T_m$ of an undesired duplex. In this case, determination of the degree of hybridization is accomplished simply by testing for the presence of hybridized probe.

Primer extension assays are commonly used for SNP typing and have can also be used in other genotyping and mutation screening applications (Pastinen T. et al., *Genome Res.*, 10:1031-42 (2000)). In the present invention, the presence of minor groove binders and, in some cases, modified bases can improve primer extension assays. For example, the added duplex stability provided by MB, or 5-substituted pyrimidine or 3-substituted pyrazolo[3,4-d]pyrimidine enables extensions to be performed at elevated temperatures. This is advantageous as problematic secondary structures in target molecules can be eliminated at elevated temperatures. Also, hybridization of target to primer is faster at higher temperature. Thermostable polymerases such as Taq polymerase and Bst DNA polymerase can be used in such reactions. While MBs and modified bases can provide probes and primers have the advantages noted above, the use of a modified base will typically be in a position other than the 3'-terminal position in order to avoid primer extension inhibition.

Furthermore, MBs and modified bases improve the specificity of assays by eliminating one class of false positive signals. Primer sequences that form hairpin structures or homodimers are prone to template-independent extension (the 5' end of the primer functions as template), resulting in false positive signal. MBs and modified bases on "templates" inhibit extension by DNA polymerases. Thus, MBs on the 5' end, or modified bases on the 5' end or middle of a primer, can prevent extension (false positives) from primer hairpins or primer dimers. Finally, PPG can be used to eliminate non-canonical structures formed by G-rich oligonucleotides, enabling primer extension assays in such sequences.

Other assays in which the present modified oligonucleotides are particularly useful are described in U.S. Pat. No. 6,312,894.

In view of the above, the present invention provides a method for continuous monitoring of polynucleotide amplification, comprising:

(a) combining a sample containing a target sequence, with one or more oligonucleotide primers complementary to regions of the target sequence, a polymerizing enzyme, nucleotide substrates, and an oligonucleotide conjugate having a formula:

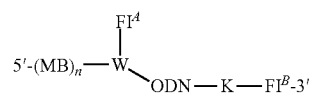

wherein MB is a minor groove binder, n is 0 or 1, one of $Fl^A$ and $Fl^B$ is a fluorophore and the other of $Fl^A$ and $Fl^B$ is a quencher, W is a trivalent linking group, ODN is an oligonucleotide or modified oligonucleotide, K is a bond or a linking group, wherein the ODN sequence overlaps from 1 to 7 bases with a primer sequence and the ODN portion has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

The present invention also provides an alternative method for continuous monitoring of polynucleotide amplification, comprising:

(a) combining a sample containing a target sequence, with one or more oligonucleotide primers complementary to regions of the target sequence, a polymerizing enzyme, nucleotide substrates, and an oligonucleotide conjugate having a formula:

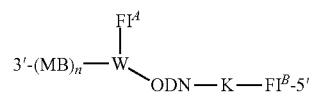

wherein MB is a minor groove binder, n is 0 or 1, one of $Fl^A$ and $Fl^B$ is a fluorophore and the other of $Fl^A$ and $Fl^B$ is a quencher, W is a trivalent linking group, ODN is an oligonucleotide or modified oligonucleotide, K is a bond or a linking group, the ODN sequence having an overlap of from 1 to 7 bases with a primer sequence and the ODN portion has a sequence complementary to a portion of the target sequence being amplified, to provide a mixture;

(b) incubating the mixture under conditions favorable for polymerization with a polymerase with 5'-nuclease activity; and (c) continuously monitoring the amplification by monitoring the fluorescence produced upon conjugate hybridization to the amplified target and cleavage by 5'-nuclease activity.

The present invention further provides a second alternative method for continuous monitoring of polynucleotide amplification, comprising:

(a) combining a sample containing a target sequence, with two oligonucleotide primers complementary to regions of the target sequence, a polymerizing enzyme, nucleotide substrates, and a double strand nucleic-acid binding dye, wherein the first primer sequence overlaps from 1 to 7 bases with the second primer sequence, to provide a mixture;

(b) incubating the mixture under conditions favorable for polymerization; and (c) continuously monitoring the amplification by monitoring the fluorescence produced upon binding of the dye to the amplified target.

In a related embodiment, the present invention provides a method for continuous monitoring of polynucleotide amplification, comprising:

(a) combining a sample containing a target sequence, with two oligonucleotide primers complementary to regions of the target sequence, a polymerizing enzyme, nucleotide substrates, and an oligonucleotide conjugate having a formula:

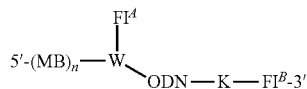

wherein MB is a minor groove binder, n is 0 or 1, one of $Fl^A$ and $Fl^B$ is a fluorophore and the other of $Fl^A$ and $Fl^B$ is a quencher, W is a trivalent linking group, ODN is an oligonucleotide or modified oligonucleotide, K is a bond or a linking group, wherein the ODN sequence overlaps from 1 to 7 bases with both primer sequences and the ODN portion has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

In an alternative method, fluorescence is measured after completion of amplification, this type of method is known as an end-point analysis method.

Amplification procedures are those in which many copies of a target nucleic acid sequence are generated, usually in an exponential fashion, by sequential polymerization Many amplification reactions, such as PCR, utilize reiterative primer-dependent polymerization reactions. A primer is a nucleic acid that is capable of hybridizing to a second, template nucleic acid and that, once hybridized, is capable of being extended by a polymerizing enzyme (in the presence of nucleotide substrates), using the second nucleic acid as a template. Polymerizing enzymes include, but are not limited to, DNA and RNA polymerases and reverse transcriptases, etc. Conditions favorable for polymerization by different polymerizing enzymes are well-known to those of skill in the art. See, for example, Sambrook et al., supra; Ausubel, et al., supra; Innis et al., supra. Generally, in order to be extendible by a polymerizing enzyme, a primer must have an unblocked 3' end, preferably a free 3' hydroxyl group. The product of an amplification reaction is an extended primer, wherein the primer has been extended by a polymerizing enzyme.

Thus, in one preferred embodiment of the invention, the methods disclosed and claimed herein are useful in improving and monitoring amplification reactions such as PCR. See, e.g., U.S. Pat. Nos. 4,683,202; 4,683,195 and 4,800,159; Mullis and Faloona, supra; and Saiki et al., supra. The polymerization step of PCR is most often catalyzed by a thermostable polymerizing enzyme, such as a DNA polymerase isolated from a thermophilic bacterium, because of the elevated temperatures required for the denaturation step of PCR.

In still another aspect, the present invention provides a method for detecting a target sequence in a polynucleotide, wherein the polynucleotide is present in a mixture of other polynucleotides, and wherein one or more of the other polynucleotides in the mixture comprise sequences that are related but not identical to the target sequence, the method comprising:

(a) contacting the mixture of polynucleotides with an oligonucleotide conjugate having the formula:

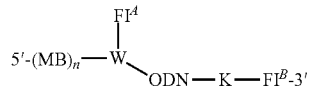

wherein MB is a minor groove binder, n is 0 or 1, one of $Fl^A$ and $Fl^B$ is a fluorophore and the other of $Fl^A$ and $Fl^B$ is a quencher, W is a trivalent linking group, ODN is an oligonucleotide or modified oligonucleotide, K is a bond or a linking group; the ODN sequence having an overlap of from 1 to 7 bases with a primer sequence and the ODN is an oligonucleotide or modified oligonucleotide, wherein the conjugate forms a stable hybrid only with said target sequence that is perfectly complementary to the ODN portion of said conjugate, and the conjugate does not form a stable hybrid with any of the other polynucleotides; and (b) measuring the fluorescence produced on hybrid formation, whereby hybrid formation indicates the presence of said target sequence.

Preferably, at least one of the other polynucleotides has a target sequence (a related sequence) with one or more base mismatches, more preferably one to three mismatches, and most preferably only one base mismatch.

The present invention also provides an alternative a method for detecting a target sequence in a polynucleotide, wherein the polynucleotide is present in a mixture of other polynucleotides, and wherein one or more of the other polynucleotides in the mixture comprise sequences that are related but not identical to the target sequence (e.g., having from one to three mismatches, preferably one or two mismatches), the method comprising:

(a) contacting the mixture of polynucleotides with two primer oligonucleotides or modified oligonucleotides, the oligonucleotide or modified oligonucleotide sequences having an overlap of from 1 to 7 bases with each other and the oligonucleotide or modified oligonucleotide form stable hybrids only with said target sequence that is perfectly complementary to the ODN portion of said primer, and the primer does not form a stable hybrid with any of the other polynucleotides; and (b) measuring the fluorescence produced on binding of a nucleic acid binding dye to amplified target, whereby dye binding indicates the presence of said target sequence.

As noted above, a target sequence refers to a nucleotide sequence which comprises a site of hybridization for a probe or a primer. Target sequences can be found in any nucleic acid including, but not limited to, genomic DNA, cDNA, RNA and any amplified product thereof, and can comprise a wild-type gene sequence, a mutant gene sequence, a non-coding sequence, a regulatory sequence, etc. A target sequence will generally be less than 100 nucleotides, preferably less than 40 nucleotides, and most preferably, less than 21 nucleotides in length.

The conjugates used in this aspect of the invention are essentially the same as those that have been described herein and the polynucleotides can be distinguished by determining which polynucleotides hybridize to the oligonucleotide conjugate. Conditions for hybridization of oligonucleotide conjugates or probes are well-known to those of skill in the art. See, for example, Sambrook et al., supra; Ausubel et al., supra; Innis et al., supra; Hames et al., supra; and van Ness et al., supra.

Hybridization can be assayed (i.e., hybridized nucleic acids can be identified) by distinguishing hybridized probe from free probe by one of several methods that are well-known to those of skill in the art. These include, but are not limited to, attachment of target nucleic acid to a solid support, either directly or indirectly (by hybridization to a second, support-bound probe or interaction between surface-bound and probe-conjugated ligands) followed by direct or indirect hybridization with probe, and washing to remove unhybridized probe; determination of nuclease resistance; buoyant density determination; affinity methods specific for nucleic acid duplexes (e.g., hydroxyapatite chromatography); interactions between multiple probes hybridized to the same target nucleic acid; etc. See, for example, Falkow et al., U.S. Pat. No. 4,358,535; Urdea et al., U.S. Pat. Nos. 4,868,105 and 5,124,246; Freifelder, *Physical Biochemistry*, Second Edition, W. H. Freeman & Co., San Francisco, 1982; Sambrook, et al., supra; Ausubel et al., supra; Hames et al., supra; and other related references. The duplex-stabilizing capability of the oligonucleotide conjugates described herein makes hybridization possible under more stringent conditions, wherein potentially occluding secondary structure in the target nucleic acid can be minimized. Accordingly, such oligonucleotide conjugates are particularly preferred in this aspect of the invention.

In one group of preferred embodiments, the oligonucleotide conjugate used in the invention method has at least one pyrazolo[3,4-d]pyrimidine and/or a 3-substituted pyrazolo[3,4-d]pyrimidine base. In this group of embodiments, the conjugate is hybridized to an extension product of a target, and a change in the physical state of the fluorophore/quencher pair is effected as a consequence of hybridization.

The use of primers, probes and conjugates (5'-MB-Fl$^A$-ODN-Fl$^B$-3') of the present invention method in this and related methods allows greater speed, sensitivity and discriminatory power to be applied to assays in challenging sequence environments. In particular, the enhanced ability of the probes and conjugates to allow discrimination between a perfect hybrid and a hybrid containing a single-base mismatch will facilitate the use of real-time amplification assays in, for example, the identification of single-nucleotide polymorphisms and the like. One of skill in the art will appreciate that compositions and methods, such as those of the invention, that are capable of discriminating single-nucleotide mismatches will also be capable of discriminating between sequences that have 2, 3, 4, 5, or even 6 or more mismatches with respect to one another.

In yet another aspect, the present invention provides a method for distinguishing between wild-type, mutant and heterozygous target polynucleotides, the method comprising:

(a) contacting a sample containing a target polynucleotide with two probes wherein a first probe is specific for the wild-type target polynucleotide and a second probe is specific for the mutant target polynucleotide, each of the probes having a formula:

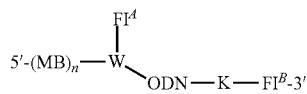

wherein MB is a minor groove binder, n is 0 or 1, one of Fl$^A$ and Fl$^B$ is a fluorophore and the other of Fl$^A$ and Fl$^B$ is a quencher, W is a trivalent linking group, ODN is an oligonucleotide or modified oligonucleotide, the ODN sequence having an overlap of from 1 to 7 bases with a primer sequence; K is a bond or a linking group; wherein the first and second probes have different fluorophores and each of the probes forms a stable hybrid only with the target sequence that is perfectly complementary to the ODN portion of the probe; and (b) measuring the fluorescence produced on hybrid formation, whereby hybrid formation indicates the presence or absence of each of the wild-type, mutant and heterozygous target polynucleotides.

In this aspect of the invention the melting temperatures ($T_m$) for each hybrid produced between the first and second probes and their respective targets are preferably within about 5° C. of each other. In one group of preferred embodiments, the ODN portion of each of the probes is an oligonucleotide or modified oligonucleotide having from 8 to 18 bases or modified bases, more preferably, an oligonucleotide or modified oligonucleotide having from 10 to 15 bases or modified bases. In other preferred embodiments, the fluorophore portions of each of the probes are selected from cyanines, BODIPY analogs, 5-FAM™, 6-FAM™, TET™, JOE™, HEX™, VIC™, NED™, TAMRA™, ROX™, Bothell Blue™ and Yakima Yellow™ (YY). These fluorophores are available from Applied Biosystems Inc., Foster City, Calif. and from Epoch Biosciences, Inc., Bothell, Wash.

In still other preferred embodiments, the ODN portion of each of said probes contains at least one modified base. Preferably, each modified base is independently selected from 6 amino 1H-pyrazolo[3,4-d]pyrimidin-4(5H)-one, 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo[3,4-d]pyrimidine-4-one, 6-amino-3-(3-hydroxyprop-1-ynyl)-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl-1,3-dihydropyrimidine-2,4-dione, 5-(3-hydroxyprop-1-ynyl)-1,3-dihydropyrimidine-2,4-dione, 6-amino-5-prop-1-ynyl-1,3-dihydropyrimidine-2-one, 6-amino-5-(3-hydroxyprop-1-yny)-1,3-dihydropyrimidine-2-one, 6-amino-5-(3-aminoprop-1-yny)-1,3-dihydropyrimidine-2-one, 5-[4-amino-3-(3-methoxyprop-1-ynyl)pyrazol[3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol, 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione, 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chloro-1H-pyrazolo[3,4-d]pyrimidin-4-ylamine.

In another aspect, the present invention provides a method for distinguishing between wild-type, mutant and heterozygous target polynucleotides, the method comprising:

(a) measuring the fluorescence emission as a function of temperature to determine a first melting profile of a first probe melting from a first amplified polynucleotide and a second melting profile of a second probe melting from a second amplified polynucleotide; and (b) comparing the first melting curve to the second melting curve.

In other preferred embodiments, the sample is further contacted with a set of primers under amplification conditions and each of the primers contains from one to ten modified bases selected from the group provided above. Accordingly, in another aspect of the invention, kits are provided that contain probes/conjugates as described above, along with primers for amplification reactions, wherein the primers contain one or more modified bases, more preferably, from one to ten modified bases per primer.

EXAMPLE 1

This example demonstrates the effect of primer and probe overlap with one to 11 base pairs on an enterovirus model.
Real-Time PCR Using MGB Eclipse Labeled Probes Real-time PCR was conducted on an ABI Prism® 7900 Sequence Detection System (SDS) (Applied Biosystems, Foster City, Calif.), (Afonina, I et al., J. Clin. Ligand Assay, Vol. 25, Vol. 23, pp. 268). 50 cycles of a three step PCR (95° C. for 5 s, 56° C. for 20 s and 76° for 30 s) profile was run, after an initial 2 min at 95° C. Commercially available 2× Jump Start™ Taq Ready Mix™ for Quantitative PCR with 5 mM final $Mg^{2+}$ concentration (Sigma #D 74403) supplemented with JumpStart Taq Polymerase (Sigma Catalog #90 4184) to a final amount of 0.37 U/μl was used. Final concentration of probes was 0.2 μM; concentration of both primers was 0.1 μM. Each 5 μl reaction contained 10 ng of template DNA or cDNA lyophilized in 96 or 384 well plates with a speed vac prior to reaction set up. Routinely DNA samples were tested in triplicates using a 384-well plate. A BIOMEK® 2000 Laboratory Automation Station (Beckman Coulter, USA) was used to setup PCR reactions.
Model System.

The primer and overlapping probe sequences for the enterovirus MGB Eclipse assay are shown in Table 2 (SEQ ID NOS:1-13).

TABLE 2

Primer and overlapping probe sequences "A*" is Super A, MGB ligand is $DPI_3$, Q is Eclipse Dark Quencher and Fl is fluorescein.

| | | Sequence |
|---|---|---|
| Forward Primer | | GTTAGGA*TTAGCCGCATTC (SEQ ID NO: 1) |
| Reverse Primer | | GA*AGA*GTCTATTGA*GCTA |
| Probe # | Overlap | |
| 1 | 0 | MGB-Q-AGTAGTCCTCCGGC-F1 (SEQ ID NO: 3) |
| 2 | 1 | MGB-Q-TCCTCCGGCCCCTG-F1 (SEQ ID NO: 4) |
| 3 | 3 | MGB-Q-CCTCCGGCCCCTGAA-F1 (SEQ ID NO: 5) |
| 4 | 4 | MGB-Q-CCTCCGGCCCCTGAAT-F1 (SEQ ID NO: 6) |
| 5 | 5 | MGB-Q-CTCCGGCCCCTGAA*TG-F1 (SEQ ID NO: 7) |
| 6 | 6 | MGB-Q-TCCGGCCCCTGAATGC-F1 (SEQ ID NO: 8) |
| 7 | 7 | MGB-Q-CCGGCCCCTGAATGCG-F1 (SEQ ID NO: 9) |
| 8 | 8 | MGB-Q-CGGCCCCTGAATGCGG-F1 (SEQ ID NO: 10) |
| 9 | 9 | MGB-Q-GGCCCCTGAATGCGGC-F1 (SEQ ID NO: 11) |
| 10 | 10 | MGB-Q-GCCCCTGAATGCGGCT-F1 (SEQ ID NO: 12) |
| 11 | 11 | MGB-Q-CCCCTGA*ATGCGGCTA-F1 (SEQ ID NO: 13) |

Figure 2:
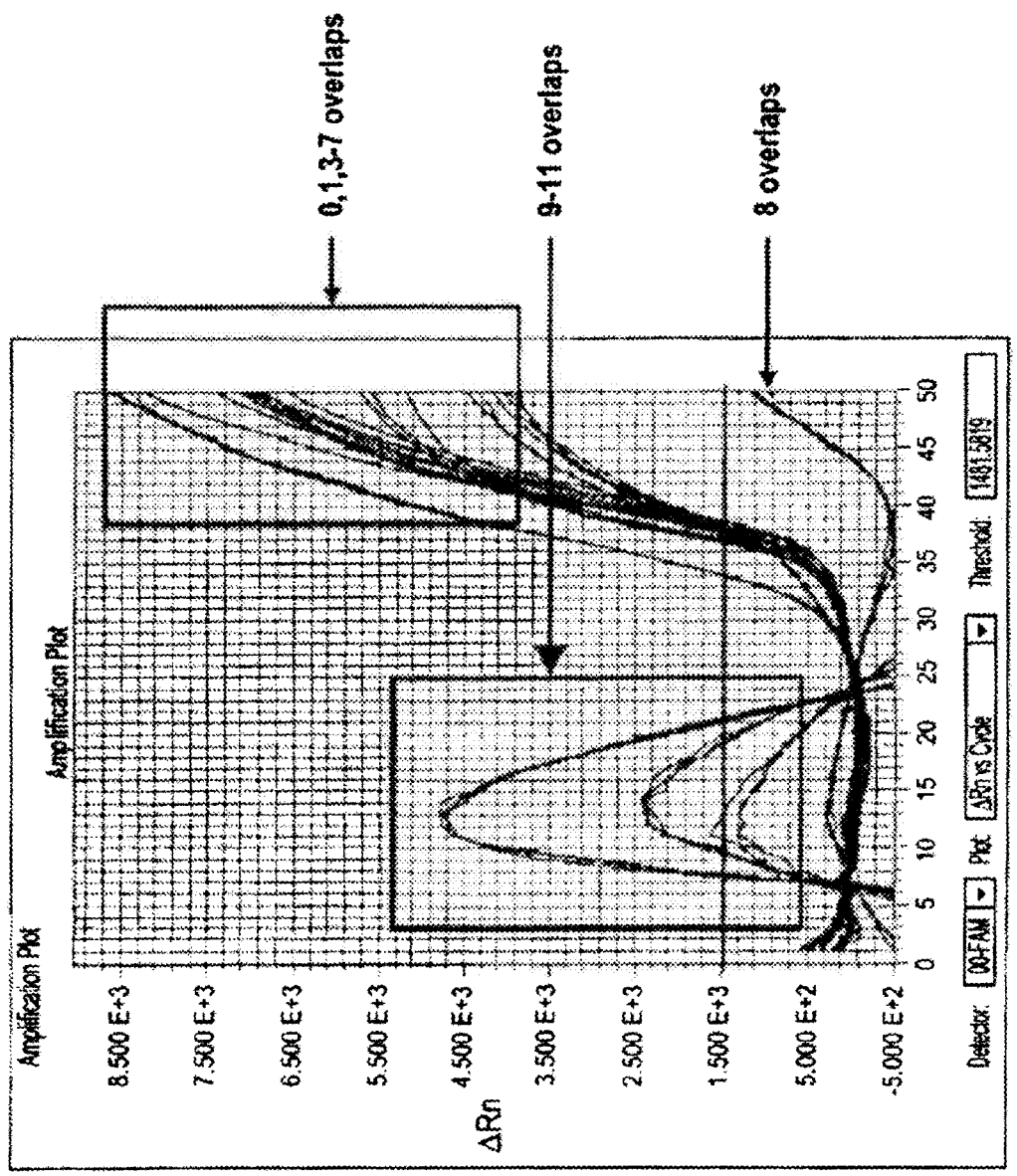
FIG. 2 provides the results of an MGB-Eclipse assay using the primers and probes provided in Table 2.

These probes were evaluated in a MGB Eclipse assay and the results are shown in FIG. 2.

As shown in FIG. 2 all the probes with 0 to 7 overlapping bases (#1 to 8) with the primer, showed amplification. The probe with a 6 base overlap (#7) gave amplification similar than that of the control with no overlaps. The signal was significantly reduced with 8 overlaps (#9) while no amplification-related signal was obtained with 9-11 overlaps (#10-12).

EXAMPLE 2

This example illustrates the detection of BK polyomavirus with a MGB Eclipse assay where a primer and probe overlaps with a single base. Probe and primers were designed against BK polyomavirus coding sequence VP1 shown. The one base overlap with the reverse primer is shown below (SEQ ID NO:14).

CCAAATAGGCCTTATGGTCAGTATTCATTACCTGGGACTGGGCTGTTGGG

TTTTTAGGGGTTATAGTACCATCAGGGTACTTTGACCTGTAATT

*cattagca ctccctgc atttcc*AAGGGTTCTCCACCTACAGCAAA

*<u>G</u>aagtggaa attactgc cttgaatagg*TTTTCCTCCACCATGCTCA

TGCACTTTTTGTGACCCTGCATGAAGGTTAAGCATGCTAGTTATTCCAAT

AACCTCTGTTTGTA

Primer sequences are shown in italics lower case in bold and the probe sequences in upper case bold. The overlapping primer and probe base is shown as bold and underlined.

Figure 3:
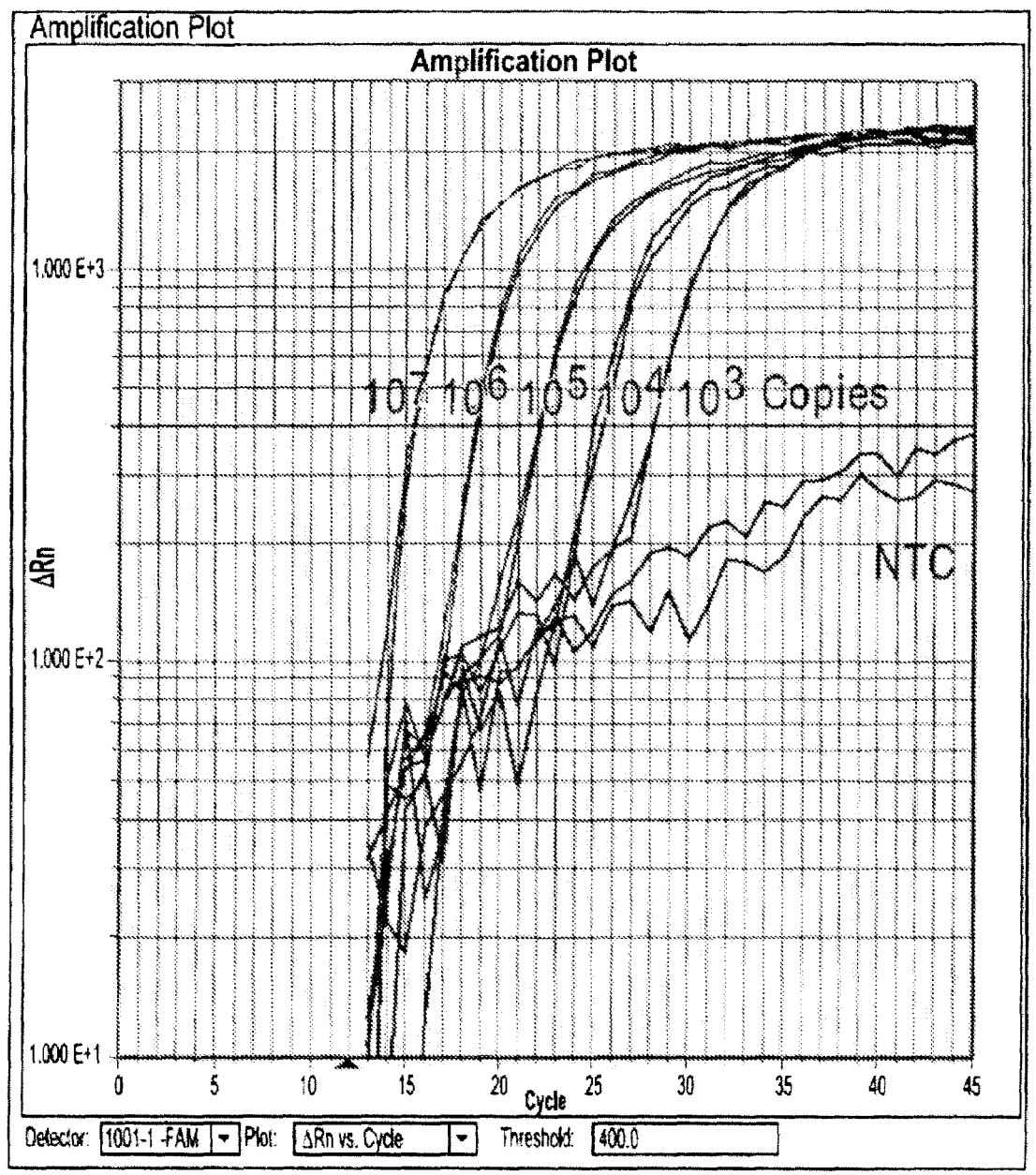
FIG. 3 provides the results of a PCR amplification of BK virus.

A titration of the BK virus from $10^3$ to $10^7$ copies with the overlapping primer and probe is shown in FIG. 3, demonstrating efficient PCR amplification. Standard MGB Eclipse Probe Assay conditions were used.

EXAMPLE 3

Illustrates a single base primer and probe overlap used in a MGB Eclipse assay for a MMP3 (matrix metalloproteinase 3 (stromelysin 1, progelatinase)) polymorphism. The probe and primer designs are shown below where "G*" is Super G. The single base overlap was designed between the reverse primer and probe. The sequences of the probes and primers are shown below (SEQ ID NOS:15-18).

Figure 4:
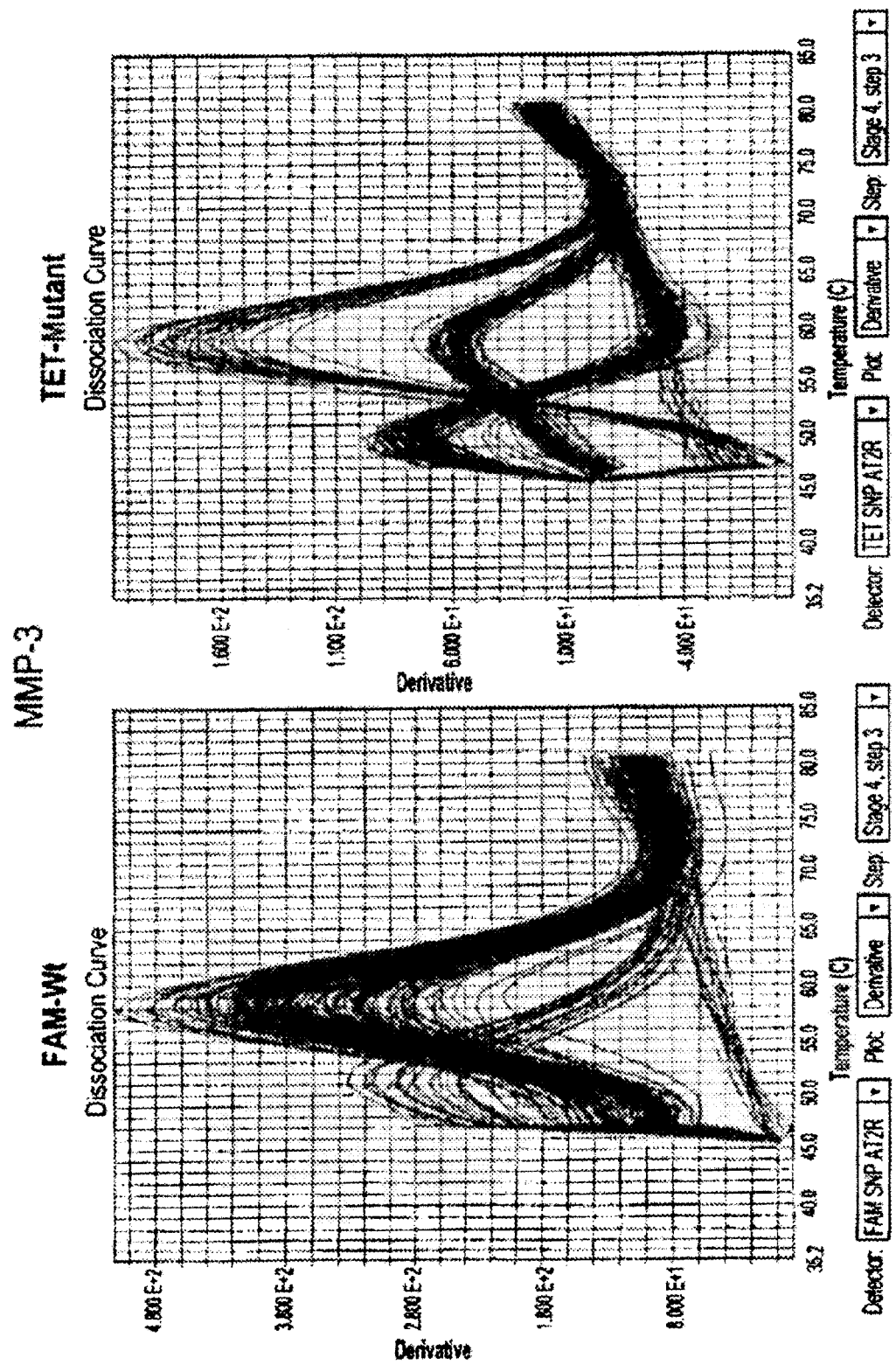
FIG. 4 provides a post PCR amplification melt curve polymorphism typing of MMP-3 polymorphism in 102 DNA samples.

(SEQ ID NO: 15)
Forward primer GCACCTGGCCTAAAGACATT (SEQ ID NO: 16)
Reverse primer CCCTGTATTTCAATCAGGACAAGA (SEQ ID NO: 17)
Wild-type probe MGB-GG*GAAAAAACCATGT-FAM (SEQ ID NO: 18)
Mutant probe MGB GG*GAAAAACCATGT-TET The PCR amplification was performed as described in Example 1 with minor modification: $Mg^{2+}$ concentration was 2 mM, annealing temperature was 52° C., and a melt step was conducted after PCR was completed in a Rotor-Gene 3000 or AB 7900. The post MGB Eclipse PCR melt curve genotyping of the polymorphism in 102 DNA samples is shown in FIG. 4. One hundred and two unrelated Centre Etude Polymorphism Humaine (CEPH) DNA samples were obtained from the Coriell Institute of Medical Research (http://locus.umdnj.edu) after specifying that the DNA samples were to be used for research use only.

FIG. 4 indicates efficient PCR amplification and satisfactory typing of wild-type, heterozygote and mutant DNA samples. Typing was confirmed by analysis of melting curves in the two channels. The observed typing was in accordance with the known allele type of each DNA sample.

EXAMPLE 4

This example illustrates a case where the two primers sequences overlap with 4 bases each of the probe sequence for an Influenza group A assay. In addition this example illustrates also endpoint measurement of fluorescence post-PCR amplification. The probe and primer designs are shown below (SEQ ID NOS:19-23):

Template:5'-AATAAATCATAA*CTCATGGAATGGCT*aaagACAAGACCAAtcct*GTCACCTCT*GAC-3'
3'- GAGTACCTTACCGATTTCTGTTCTGGTT*AGGACAGTGGAGACTG*AATACTAAATAA-5'
(SEQ ID NOS: 19-20)

Forward Primer: AATAAATCATAAGTCAGA*GGTGACagga     $T_m$ 67.8° C. (65.6° C.),

Reverse Primer: AATAAATCATAACTCA*TGGA*ATGGCTaaag     $T_m$ 67.8° C. (65.4° C.)
(SEQ ID NOS: 21-22)

Probe: MGB-F1-**AAAGACAA*GACCAA**tcct-Q     $T_m$ 70.2° C.
(SEQ ID NO: 23)

In the template sequence above, the probe sequence is shown in bold uppercase, with the overlapping sequence in the probe shown in lower case. The primer sequences are shown in upper case italics, with the overlapping sequence in the primer with the probe sequence shown in bold lower case italics and the flap sequence underlined. MGB is the minor groove binder ligand, A* is Super A base, Fl is Gig Harbor Green and Q is the Eclipse Dark Quencher.

Figure 5:
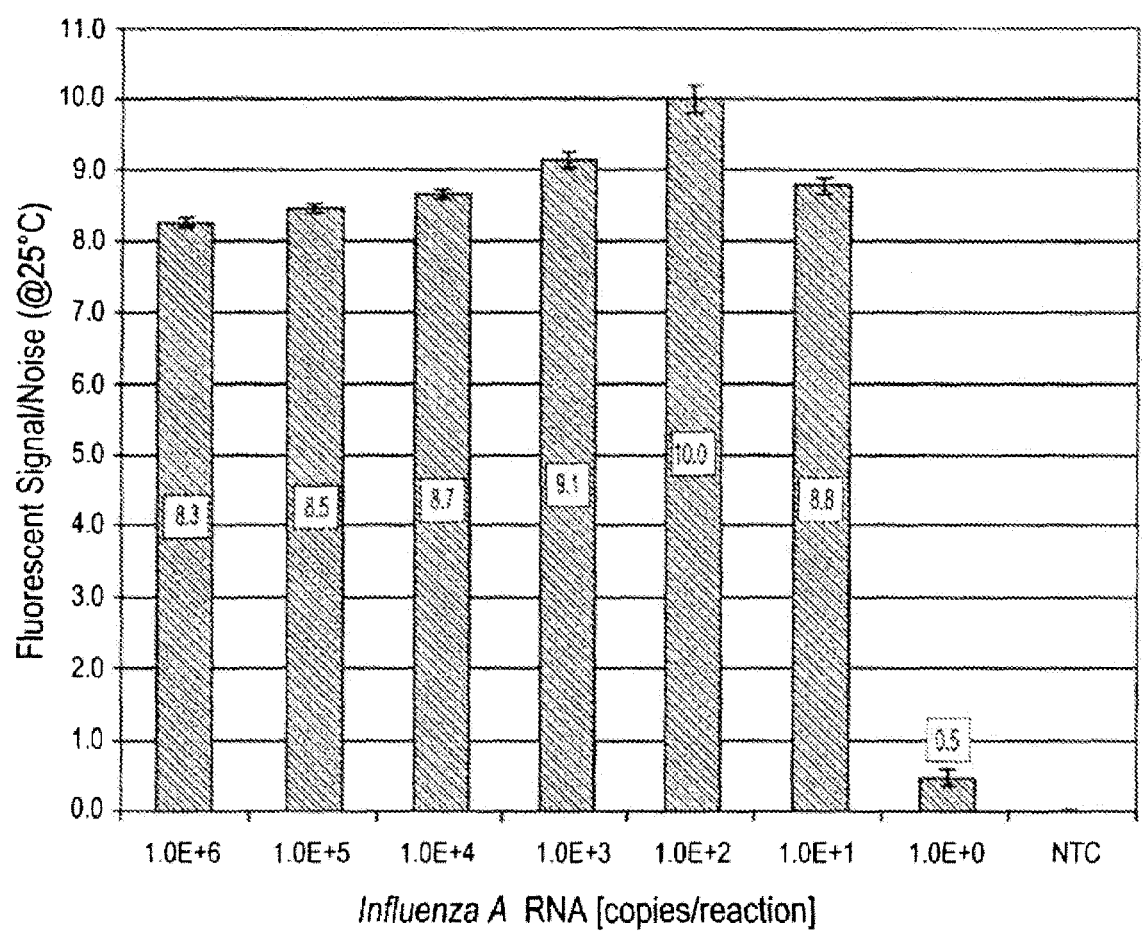
FIG. 5 provides the fluorescent signal/noise ratio from a post-PCR plate, read at 25° C. on an ABI 7900 for different Influenza A RNA concentrations.

RT-PCR was performed with the one-step Qiagen, QuantiTect master mix containing 4 mM MgCl$_2$ to which was add 15.2 U of Ambion (Austin, Tx) RNase inhibitor and the final concentration of probe, and primers in a 15 μl assay volume were respectively, 200 nM and 1 μM. The RT was performed at 60° C. for 15 mM, and the PCR 15 min at 95° C. then cycled at 95° C. for 5 seconds, at 56° C. for 20 sec and at 76° C. for 15 seconds. Fluorescence emission was measure post PCR amplification in an ABI PRISM® 7900HT Sequence Detection System (Foster City, Calif.). The signal to noise ratios for a titration curve from $1\times10^6$ to $1\times10^0$ copies of Influenza A RNA is shown in FIG. 5. As indicated titration curves from $1\times10^6$ to $1\times10^1$ copies of Influenza A RNA showed fluorescent signal to noise ratio that varied from 8.2 to 10. Even the $1\times10^0$ dilution could be distinguished form the no template control (NTC).

One of ordinary skill in the art will recognize from the provided description, figures, and examples, that modifications and changes can be made to the various embodiments of the invention without departing from the scope of the invention defined by the following claims and their equivalents. All references to patents, patent applications and publications are incorporated herein by reference in their entirety.

What is claimed is:

1. A method for detecting polynucleotide amplification of a target sequence, comprising:
   (a) providing a mixture comprising a sample containing a target sequence, with one or more than one oligonucleotide primers complementary to regions of the target sequence, a polymerizing enzyme, nucleotide substrates, and an oligonucleotide probe comprising a 5' end and a 3' end and two or more labels, wherein the oligonucleotide probe is an oligonucleotide conjugate, wherein one of the labels is a fluorophore and one of the labels is a quencher, wherein the oligonucleotide conjugate comprises an oligonucleotide or a modified oligonucleotide, wherein the oligonucleotide or modified oligonucleotide sequence has an overlap of from 1 to 7 bases with at least one of said primer sequences and the oligonucleotide or modified oligonucleotide has a sequence complementary to a portion of the target sequence being amplified;
   (b) incubating the mixture under conditions favorable for polymerization and amplification of the target sequence; and
   (c) detecting the amplification of the target sequence.

2. The method of claim 1, wherein the oligonucleotide conjugate comprises a modified oligonucleotide comprising at least one modified base.

3. The method of claim 2, wherein said at least one modified base is a base attached to a peptide nucleic acid (PNA) or a base attached to a locked nucleic acid.

4. The method of claim 3, wherein said modified base is a base attached to PNA.

5. The method of claim 3, wherein said modified base is a base attached to a locked nucleic acid.

6. The method of claim 2, wherein the modified base is selected from the group consisting of 6-amino-1H-pyrazolo[3,4 d]pyrimidin 4(5H)-one (PPG), 4-amino-1H -pyrazolo[3,4 d]pyrimidine (PPA) and 1H-pyrazolo[5,4 d]pyrimidin 4(5H)-6(7H)-dione (ppX).

7. The method of claim 2, wherein the modified base is selected from the group consisting of 6-amino-3-prop-1-ynyl-5-hydropyrazolo[3,4-d]pyrimidine-4-one (PPPG), 6-amino-3-(3-hydroxyprop-1-ynyl)1-5-hydropyrazolo[3,4-d]pyrimidine-4-one (HOPPPG), 6-amino-3-(3-aminoprop-1-ynyl)-5-hydropyrazolo[3,4-d]pyrimidine--4-one (NH$_2$PPPG), 4-amino-3-(prop-1-ynyl)pyrazolo[3,4-d]pyrimidine (PPPA), 4-amino-3-(3-hydroxyprop-1-ynyl)pyrazolo[3,4-d]pyrimidine (HOPPPA), 4-amino-3-(3-aminoprop-1-ynyl)pyrazolo[3,4-d]pyrimidine (NH$_2$PPPA), 3-prop-1-ynylpyrazolo[3,4-d]pyrimidine-4,6-diamino ((NH$_2$)$_2$PPPA), 2-(4,6-diaminopyrazolo[3,4-d]pyrimidin-3-yl)ethyn-1-ol, ((NH$_2$)$^2$PPPAOH), 3-(2-aminoethynyl)pyrazolo[3,4-d]pyrimidine-4,6-diamine, ((NH$_2$)$_2$PPPANH$_2$), 5-prop-1-ynyl-1,3-dihydropyrimidine-2,4-dione (PU), 5-(3-hydroxyprop-1-ynyl)-1,3-dihydropyrimidine-2,4-dione (HOPU), 6-amino-5-prop-1-ynyl-3-dihydropyrimidine-2-one (PC), 6-amino-5-(3-hydroxyprop-1-yny)-1,3-dihydropyrimidine-2-one (HOPC), 6-amino-5-(3-aminoprop-1-yny)-1,3-dihydropyrimidine-2-one (NH$_2$PC), 5-[4-amino-3-(3-methoxyprop-1-ynyl)pyrazol[3,4-d]pyrimidinyl]-2-(hydroxy-methyl)oxolan-3-ol (CH$_3$OPPPA), 6-amino-1-[4-hydroxy-5-(hydroxymethyl)oxolan-2-yl]-3-(3-methoxyprop-1-yny-1)-5-hydropyrazolo[3,4-d]pyrimidin-4-one (CH$_3$OPPPG), 4,(4,6-Diamino-1H-pyrazolo[3,4-d]pyrimidin-3-yl)-but-3-yn-1-ol (Super A), 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione (Super T), 3-iodo-1H-pyrazolo[3,4-d]pyrimidine-4,6-diamine ((NH$_2$)$_2$PPAI), 3-bromo-1H-pyrazolo[3,4-d]pyrimidine-4,6-diamine ((NH$_2$)$_2$PPABr), 3-chloro-1H-pyrazolo[3,4-d]pyrimidine-4,6-diamine ((NH$_2$)$_2$PPACl), 3-Iodo-1H-pyrazolo[3,4-d]pyrimidin-4-ylamine (PPAI), 3-Bromo-1H-pyrazolo[3,4-d]pyrimidin-4-ylamine (PPABr) and 3-chloro-1H-pyrazolo[3,4-d]pyrimidin-4-ylamine (PPACl).

8. The method of claim 1, wherein the fluorophore has an emission wavelength of from about 400 nm to about 800 nm and is selected from the group consisting of coumarins, resorufins, xanthenes, naphthyamines, cyanines, rhodamines, acridines and bodipy analogs.

9. The method of claim 1, wherein the fluorophore selected from the group consisting of cyanines, BODIPY analogs, 5-FAM, 6-FAM, TET™, JOE™ HEX™, VIC™, NED™, TAMRA™, ROX™, Bothell Blue™ and Yakima Yellow™ (YY).

10. The method of claim 1, wherein the quencher has an absorption maximum of from about 400 nm to about 800 nm and is selected from the group consisting of bis azo dyes, dabcyl, TAMRA and carboxytetramethyl rhodamine.

11. The method of claim 1, wherein the incubating step is carried out in the presence of a polymerase with 5'-nuclease activity and the detecting step comprises continuously monitoring the amplification by monitoring fluorescence produced upon conjugate hybridization to an amplified target and cleavage by 5'-nuclease activity.

12. A kit for detecting nucleic acid amplification, said kit comprising:
   (a) a plurality of oligonucleotide primers complementary to regions of a target sequence;
   (b) a polymerizing enzyme;
   (c) a plurality of nucleotide substrates; and
   (d) an oligonucleotide probe comprising a 5' end and a 3' end and two or more labels, wherein the oligonucleotide probe is an oligonucleotide conjugate, wherein one of the labels is a fluorophore and one of the labels is a quencher, wherein the oligonucleotide conjugate comprises an oligonucleotide or a modified oligonucleotide, wherein the oligonucleotide or modified oligonucleotide sequence has an overlap of from 1 to 7 bases with at least one of said primer sequences and the oligonucleotide or modified oligonucleotide has a sequence complementary to a portion of the target sequence being amplified.

\* \* \* \* \*

SEQUENCE LISTING

```
<160> NUMBER OF SEQ ID NOS: 23

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:enterovirus
      Forward Primer
<220> FEATURE:
<221> NAME/KEY: modified_base
<222> LOCATION: (7)
<223> OTHER INFORMATION:
      n = 4,(4,6-diamino-1H-pyrazolo[3,4-d]pyrimidin-3-yl)-but-3-yn-1-ol
      (Super A)

<400> SEQUENCE: 1
gttaggntta gccgcattc                                                   19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:enterovirus
      Reverse Primer
<220> FEATURE:
<221> NAME/KEY: modified_base
<222> LOCATION: (2)
<223> OTHER INFORMATION: n = 4,(4,6-diamino-1H-pyrazolo[3,4-d]
      pyrimidin-3-yl)-but-3-yn-1-ol (Super A)
<220> FEATURE:
<221> NAME/KEY: modified_base
<222> LOCATION: (5)
<223> OTHER INFORMATION: n = 4,(4,6-diamino-1H-pyrazolo[3,4-d]
      pyrimidin-3-yl)-but-3-yn-1-ol (Super A)
<220> FEATURE:
<221> NAME/KEY: modified_base
<222> LOCATION: (14)
<223> OTHER INFORMATION: n = 4,(4,6-diamino-1H-pyrazolo[3,4-d]
``` pyrimidin-3-yl)-but-3-yn-1-ol (Super A)

<400> SEQUENCE: 2
gnagngtcta ttgngcta                                              18

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence:enterovirus
      Probe #1
<220> FEATURE:
<221> NAME/KEY: modified_base
<222> LOCATION: (1)
<223> OTHER INFORMATION: n = a conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (14)
<223> OTHER INFORMATION: n = c conjugated to fluorescein (Fl)

<400> SEQUENCE: 3
ngtagtcctc cggn                                                  14

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence:enterovirus
      overlapping Probe #2
<220> FEATURE:
<221> NAME/KEY: modified_base
<222> LOCATION: (1)
<223> OTHER INFORMATION: n = t conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (14)
<223> OTHER INFORMATION: n = g conjugated to fluorescein (Fl)

<400> SEQUENCE: 4
ncctccggcc cctn                                                  14

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:enterovirus
      overlapping Probe #3
<220> FEATURE:
<221> NAME/KEY: modified_base
<222> LOCATION: (1)
<223> OTHER INFORMATION: n = c conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (15)
<223> OTHER INFORMATION: n = a conjugated to fluorescein (Fl)

<400> SEQUENCE: 5
nctccggccc ctgan                                                 15

<210> SEQ ID NO 6

```
<211> LENGTH: 16
<212> TYPE: DNA
<213> ORGANISM: Artificial Sequence
<220> FEATURE:
<223> OTHER INFORMATION: Description of Artificial Sequence:enterovirus
      overlapping Probe #4
<220> FEATURE:
<221> NAME/KEY: modified_base
<222> LOCATION: (1)
<223> OTHER INFORMATION: n = c conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (16)
<223> OTHER INFORMATION: n = t conjugated to fluorescein (Fl)

<400> SEQUENCE: 6
nctccggccc ctgaan                                                   16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence:enterovirus
      overlapping Probe #5
<220> FEATURE:
<221> NAME/KEY: modified_base
<222> LOCATION: (1)
<223> OTHER INFORMATION: n = c conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (14)
<223> OTHER INFORMATION: n = 4,(4,6-diamino-1H-pyrazolo[3,4-d]
      pyrimidin-3-yl)-but-3-yn-1-ol (Super A)
<220> FEATURE:
<221> NAME/KEY: modified_base
<222> LOCATION: (16)
<223> OTHER INFORMATION: n = g conjugated to fluorescein (Fl)

<400> SEQUENCE: 7
ntccggcccc tgantn                                                   16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence:enterovirus
      overlapping Probe #6
<220> FEATURE:
<221> NAME/KEY: modified_base
<222> LOCATION: (1)
<223> OTHER INFORMATION: n = t conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (16)
<223> OTHER INFORMATION: n = c conjugated to fluorescein (Fl)

<400> SEQUENCE: 8
nccggcccct gaatgn                                                   16

<210> SEQ ID NO 9
<211> LENGTH: 16
<212> TYPE: DNA
<213> ORGANISM: Artificial Sequence
```

```
<220> FEATURE:
<223> OTHER INFORMATION: Description of Artificial Sequence:enterovirus
      overlapping Probe #7
<220> FEATURE:
<221> NAME/KEY: modified_base
<222> LOCATION: (1)
<223> OTHER INFORMATION: n = c conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (16)
<223> OTHER INFORMATION: n = g conjugated to fluorescein (Fl)

<400> SEQUENCE: 9
ncggcccctg aatgcn                                                   16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence:enterovirus
      overlapping Probe #8
<220> FEATURE:
<221> NAME/KEY: modified_base
<222> LOCATION: (1)
<223> OTHER INFORMATION: n = c conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (16)
<223> OTHER INFORMATION: n = g conjugated to fluorescein (Fl)

<400> SEQUENCE: 10
nggcccctga atgcgn                                                   16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence:enterovirus
      overlapping Probe #9
<220> FEATURE:
<221> NAME/KEY: modified_base
<222> LOCATION: (1)
<223> OTHER INFORMATION: n = g conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (16)
<223> OTHER INFORMATION: n = c conjugated to fluorescein (Fl)

<400> SEQUENCE: 11 ngccctgaa tgcggn                                                    16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:enterovirus
      overlapping Probe #10
<220> FEATURE:
<221> NAME/KEY: modified_base
<222> LOCATION: (1)
<223> OTHER INFORMATION: n = g conjugated to Eclipse Dark Quencher (Q)
      and pyrrolo[4,5-e]indolin-7-yl}carbonyl)pyrrolo[4,5-e]
``` indolin-7-yl]carbonyl}pyrrolo[4,5-e]indolin-7-
        carboxylate (DPI-3)
<220> FEATURE:
<221> NAME/KEY: modified_base
<222> LOCATION: (16)
<223> OTHER INFORMATION: n = t conjugated to fluorescein (Fl)

<400> SEQUENCE: 12 nccccctgaat gcggcn                                                      16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence:enterovirus
      overlapping Probe #11
<220> FEATURE:
<221> NAME/KEY: modified_base
<222> LOCATION: (1)
<223> OTHER INFORMATION: n = c conjugated to Eclipse Dark Quencher (Q)
      and pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (7)
<223> OTHER INFORMATION: n = 4,(4,6-diamino-1H-pyrazolo[3,4-d]
      pyrimidin-3-yl)-but-3-yn-1-ol (Super A)
<220> FEATURE:
<221> NAME/KEY: modified_base
<222> LOCATION: (16)
<223> OTHER INFORMATION: n = a conjugated to fluorescein (Fl)

<400> SEQUENCE: 13
nccctgnatg cggctn                                                       16

<210> SEQ ID NO 14
<211> LENGTH: 249
<212> TYPE: DNA
<213> ORGANISM: Artificial Sequence
<220> FEATURE:
<223> OTHER INFORMATION: Description of Artificial Sequence:BK
      polyomavirus coding sequence VP1 overlapping primer and probe

<400> SEQUENCE: 14
ccaaataggc cttatggtca gtattcatta cctgggactg ggctgttggg ttttaggggg       60
ttatagtacc atcagggtac tttgacctgt aattcattag cactccctgc atttccaagg     120
gttctccacc tacagcaaag aagtggaaat tactgccttg aataggttttt cctccaccat    180 gctcatgcac tttttgtgac cctgcatgaa ggttaagcat gctagttatt ccaataaacct   240 ctgtttgta                                                              249

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:matrix
      metalloproteinase 3 (MMP3) polymorphism Forward
      primer

<400> SEQUENCE: 15
gcacctggcc taaagacatt                                                   20

<210> SEQ ID NO 16
<211> LENGTH: 24
<212> TYPE: DNA
<213> ORGANISM: Artificial Sequence

```
<220> FEATURE:
<223> OTHER INFORMATION: Description of Artificial Sequence:matrix
      metalloproteinase 3 (MMP3) polymorphism Reverse
      primer

<400> SEQUENCE: 16
ccctgtattt caatcaggac aaga                                            24

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence:matrix
      metalloproteinase 3 (MMP3) polymorphism wild-type
      probe
<220> FEATURE:
<221> NAME/KEY: modified_base
<222> LOCATION: (1)
<223> OTHER INFORMATION: n = g conjugated to
      pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (2)
<223> OTHER INFORMATION: n = 6-amino-1H-pyrazolo[3,4-d]pyrimidin-4
      (5H)-one (ppG, PPG or Super G)
<220> FEATURE:
<221> NAME/KEY: modified_base
<222> LOCATION: (15)
<223> OTHER INFORMATION: n = t conjugated to FAM

<400> SEQUENCE: 17
nngaaaaaac catgn                                                      15

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence:matrix
      metalloproteinase 3 (MMP3) polymorphism mutant
      probe
<220> FEATURE:
<221> NAME/KEY: modified_base
<222> LOCATION: (1)
<223> OTHER INFORMATION: n = g conjugated to
      pyrrolo[4,5-e]indolin-7-yl}carbonyl)pyrrolo[4,5-e]
      indolin-7-yl]carbonyl}pyrrolo[4,5-e]indolin-7-
      carboxylate (DPI-3)
<220> FEATURE:
<221> NAME/KEY: modified_base
<222> LOCATION: (2)
<223> OTHER INFORMATION: n = 6-amino-1H-pyrazolo[3,4-d]pyrimidin-4
      (5H)-one (ppG, PPG or Super G)
<220> FEATURE:
<221> NAME/KEY: modified_base
<222> LOCATION: (14)
<223> OTHER INFORMATION: n = t conjugated to TET

<400> SEQUENCE: 18
nngaaaaacc atgn                                                       14

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence:Influenza
      group A template

<400> SEQUENCE: 19
```

```
aataaatcat aactcatgga atggctaaag acaagaccaa tcctgtcacc tctgac        56
```

<210> SEQ ID NO 20
<211> LENGTH: 56
<212> TYPE: DNA
<213> ORGANISM: Artificial Sequence
<220> FEATURE:
<223> OTHER INFORMATION: Description of Artificial Sequence:Influenza
      group A template

<400> SEQUENCE: 20

```
aataaatcat aagtcagagg tgacaggatt ggtcttgtct ttagccattc catgag        56
```

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:Influenza
      group A Forward Primer
<220> FEATURE:
<221> NAME/KEY: modified_base
<222> LOCATION: (18)
<223> OTHER INFORMATION: n = 4,(4,6-diamino-1H-pyrazolo[3,4-d]
      pyrimidin-3-yl)-but-3-yn-1-ol (Super A)

<400> SEQUENCE: 21

```
aataaatcat aagtcagngg tgacagga                                       28
```

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:Influenza
      group A Reverse Primer
<220> FEATURE:
<221> NAME/KEY: modified_base
<222> LOCATION: (16)
<223> OTHER INFORMATION: n = 4,(4,6-diamino-1H-pyrazolo[3,4-d]
      pyrimidin-3-yl)-but-3-yn-1-ol (Super A)
<220> FEATURE:
<221> NAME/KEY: modified_base
<222> LOCATION: (20)
<223> OTHER INFORMATION: n = 4,(4,6-diamino-1H-pyrazolo[3,4-d]
      pyrimidin-3-yl)-but-3-yn-1-ol (Super A)

<400> SEQUENCE: 22

```
aataaatcat aactcntggn atggctaaag                                     30
```

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:Influenza
      group A Probe
<220> FEATURE:
<221> NAME/KEY: modified_base
<222> LOCATION: (1)
<223> OTHER INFORMATION: n = a conjugated to minor groove binder ligand
      (MGB) and Gig Harbor Green (Fl)
<220> FEATURE:
<221> NAME/KEY: modified_base
<222> LOCATION: (8)
<223> OTHER INFORMATION: n = 4,(4,6-diamino-1H-pyrazolo[3,4-d]
      pyrimidin-3-yl)-but-3-yn-1-ol (Super A)
<220> FEATURE:
<221> NAME/KEY: modified_base
<222> LOCATION: (18)

```
<223> OTHER INFORMATION: n = t conjugated to Eclipse Dark Quencher (Q)

<400> SEQUENCE: 23
naagacanga ccaatccn                                                   18
```